US011774403B2

(12) United States Patent
Shimizu et al.

(10) Patent No.: US 11,774,403 B2
(45) Date of Patent: Oct. 3, 2023

(54) GAS SENSOR CONTROL DEVICE

(71) Applicant: DENSO CORPORATION, Kariya (JP)

(72) Inventors: Shoki Shimizu, Kariya (JP); Ryozo Kayama, Kariya (JP); Yuki Murayama, Kariya (JP)

(73) Assignee: DENSO CORPORATION, Kariya (JP)

( * ) Notice: Subject to any disclaimer, the term of this patent is extended or adjusted under 35 U.S.C. 154(b) by 773 days.

(21) Appl. No.: 16/782,404

(22) Filed: Feb. 5, 2020

(65) Prior Publication Data

US 2020/0264127 A1 Aug. 20, 2020

(30) Foreign Application Priority Data

Feb. 19, 2019 (JP) ................................ 2019-027504

(51) Int. Cl.

*G01N 27/419* (2006.01)
*G01N 27/407* (2006.01)
*G01N 27/406* (2006.01)
*G01N 27/41* (2006.01)
*G01N 33/00* (2006.01)

(52) U.S. Cl.

CPC ....... *G01N 27/419* (2013.01); *G01N 27/4067* (2013.01); *G01N 27/4074* (2013.01); *G01N 27/41* (2013.01); *G01N 33/0037* (2013.01)

(58) Field of Classification Search

CPC ............. G01N 27/419; G01N 27/4067; G01N 27/4074; G01N 27/41; G01N 33/0037; Y02A 50/20

See application file for complete search history.

(56) References Cited

U.S. PATENT DOCUMENTS

| | | | | |
|---|---|---|---|---|
| 6,453,724 B1 * | 9/2002 | Kawase | G01N 27/4067 73/23.31 |
| 2002/0050455 A1 | 5/2002 | Kurokawa et al. | |
| 2002/0104758 A1 * | 8/2002 | Mizutani | G01N 27/419 204/427 |
| 2004/0074773 A1 * | 4/2004 | Niwa | G01N 27/419 204/426 |
| 2015/0034484 A1 * | 2/2015 | Nakasone | G01N 27/419 204/412 |
| 2017/0219516 A1 * | 8/2017 | Toudou | G01N 27/4067 |

FOREIGN PATENT DOCUMENTS

| | | | |
|---|---|---|---|
| JP | 2004-198351 | 7/2004 | |
| WO | WO-2015029842 A1 * | 3/2015 | G01N 27/4071 |

* cited by examiner

*Primary Examiner* — Joshua L Allen
*Assistant Examiner* — Shizhi Qian
(74) *Attorney, Agent, or Firm* — Nixon & Vanderhye P.C.

(57) ABSTRACT

A first cell includes a first electrode in a measurement gas chamber and a second electrode in a reference gas chamber. A second cell includes a third electrode in the measurement gas chamber and a fourth electrode in the reference gas chamber to cause a current therebetween that corresponds to a concentration of a specific gas component in detected gas in the measurement chamber. A controller selectively implements a normal control and a reduction control. The normal control is to apply a lower voltage to the first electrode and the second electrode to remove oxygen from the detected gas. The reduction control is to apply a higher voltage to the first electrode and the second electrode to reduce the third electrode that is oxidized. The controller prohibits implementation of the reduction control on determination that implementation of the reduction control.

16 Claims, 11 Drawing Sheets

GAS SENSOR CONTROL DEVICE

CROSS REFERENCE TO RELATED APPLICATION

The present application claims the benefit of priority from Japanese Patent Application No. 2019-027504 filed on Feb. 19, 2019. The entire disclosures of all of the above applications are incorporated herein by reference.

TECHNICAL FIELD

The present disclosure relates to a gas sensor control device.

BACKGROUND

A vehicle is equipped with a gas sensor to detect a concentration of nitrogen oxide (NOx) contained in exhaust gas.

SUMMARY

According to an aspect of the present disclosure, a first cell includes a first electrode, which is provided in a measurement gas chamber configured to introduce gas to be detected, and a second electrode, which is provided in a reference gas chamber configured to introduce reference gas. The first cell is configured, on application of a voltage between the first electrode and the second electrode on the gas to be detected to remove oxygen in the gas to be detected. A second cell includes a third electrode, which is provided in the measurement gas chamber, and a fourth electrode, which is provided in the reference gas chamber. The second cell is configured, on application of a voltage between the third electrode and the fourth electrode, to cause a current to flow between the third electrode and the fourth electrode. The current corresponds to a concentration of a specific gas component in the gas to be detected after the oxygen is removed by the first cell. A controller is configured to selectively implement a normal control, which is to apply a first voltage to the first electrode and the second electrode of the first cell in order to remove oxygen in the gas to be detected, and a reduction control, which is to apply a second voltage higher than the first voltage to the first electrode and the second electrode of the first cell in order to reduce the third electrode that is oxidized.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

Figure 1:
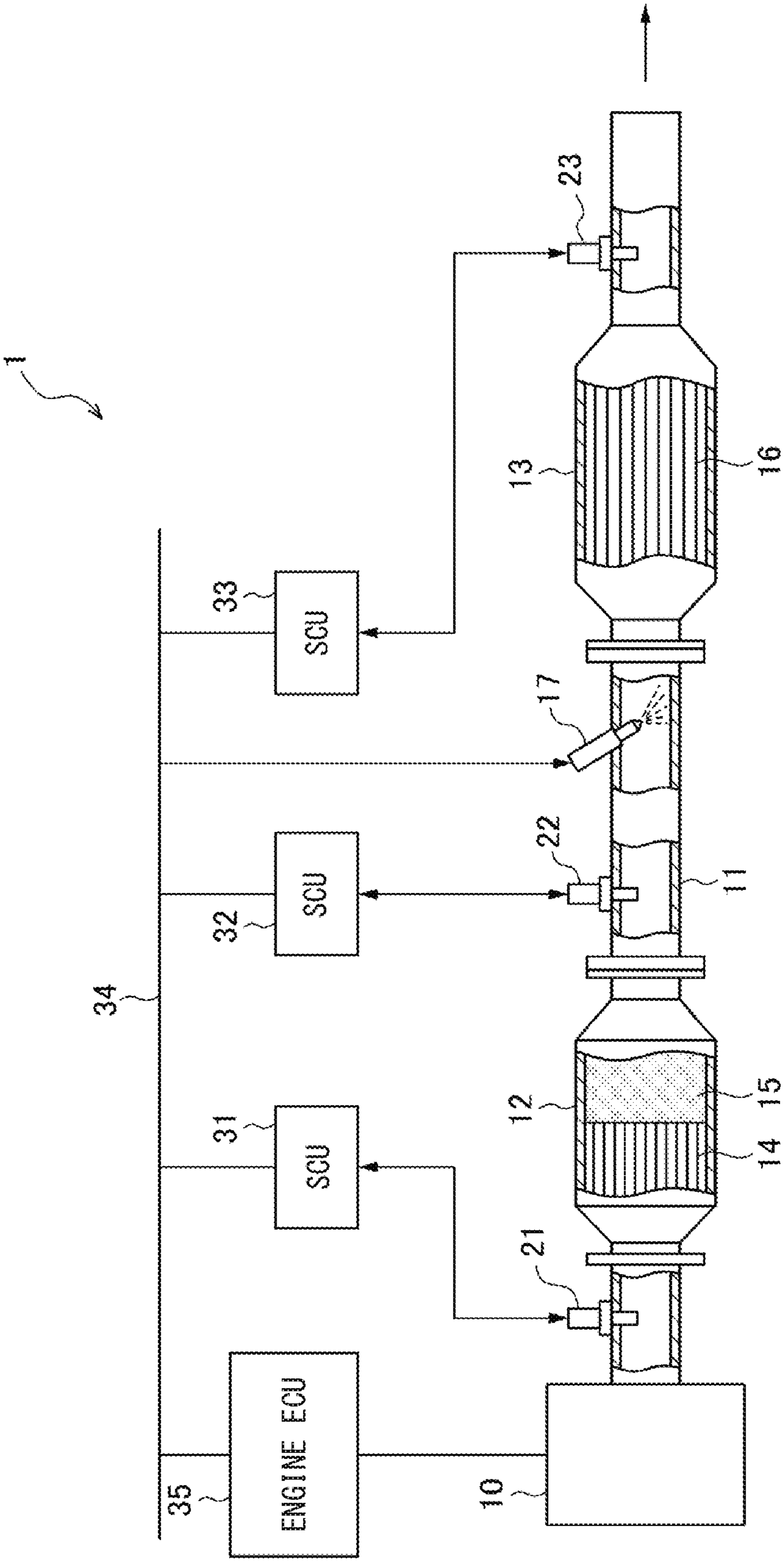
FIG. 1 is a block diagram showing a schematic configuration of an exhaust purification system for a vehicle.

To begin with, examples of the present disclosure will be described. A gas sensor according to an example of the present disclosure is provided to a vehicle to detect a concentration of nitrogen oxide (NOx) contained in exhaust gas. The gas sensor according to the example of the present disclosure includes a measurement gas chamber into which exhaust gas is drawn and a reference gas chamber into which air is drawn. The gas sensor includes a pump cell and a sensor cell. The pump cell includes a pump electrode placed in the measurement gas chamber, a common electrode placed in the reference gas chamber, and a solid electrolyte body provided between the pump electrode and the common electrode. The pump cell removes oxygen in the exhaust gas drawn into the measurement gas chamber. The sensor cell includes a sensor electrode placed in the measurement gas chamber, a common electrode placed in the reference gas chamber, and a solid electrolyte body provided between the sensor electrode and the common electrode. The pump cell removes oxygen from the exhaust gas. A sensor current flows between the electrodes of the sensor cell correspondingly to the NOx concentration in the exhaust gas from which oxygen has been removed by the pump cell. The gas sensor includes a sensor controller (SCU) that detects the NOx concentration in the exhaust gas based on the sensor current flowing between the electrodes of the sensor cell.

It is noted that, in a configuration of the gas sensor in which the sensor electrode is formed of a material that contains platinum and rhodium, it is assumable that the sensor electrode may be oxidized particularly in a situation where the gas sensor is not used. When oxygen is occluded in the sensor electrode due to oxidation, it is concerned that the NOx concentration detected by the sensor cell could vary in a period from when the operation of the gas sensor is started until when the oxygen occluded in the sensor electrode is removed.

Therefore, according to an example of the present disclosure, it is assumable to cause the SCU to implement a reduction control to apply a higher removal voltage than a usual voltage between the electrodes of the pump cell in the gas sensor in a start-up state before detection of the NOx concentration in the exhaust gas with the sensor cell. The application of the removal voltage to the pump cell decomposes water that resides in the measurement gas chamber to generate hydrogen as a reducing gas. This hydrogen adheres to the sensor electrode of the sensor cell, thereby to remove the oxygen stored in the sensor electrode quickly, and therefore to enable to reduce a time required to stably detect the NOx concentration after starting the sensor cell.

It is further noted that, in a configuration of the gas sensor according to the above example to implement the reduction control as described above at the start of the gas sensor, the following concerns may arise. For example, when the engine is restarted after an idling stop operation of the engine, the power supply voltage supplied from a vehicle battery to the gas sensor may temporarily decrease unintentionally, and subsequently, the power supply voltage of the gas sensor may be resumed several milliseconds later. The decrease in the power supply voltage of the gas sensor in such a manner may cause the SCU to reset itself and thereafter to restart subsequent to the resetting. According to an assumable configuration, the gas sensor may implement the reduction control even in a case were the SCU restarts due to the temporary decrease in the power supply voltage. It is further noted that, in such a state, the sensor electrode has not been oxidized. Therefore, the reduction control causes the pump cell to generate the hydrogen, and the hydrogen as generated rather could disable the sensor cell for proper detection of NOx in the exhaust gas. Specifically, the sensor cell is disabled for detection of NOx in the exhaust gas during a period from the start of the reduction control until hydrogen in the measurement gas chamber is removed. As described above, because of the implementation of the reduction control when the engine is restarted after the idling stop operation, the activation time of the gas sensor may be prolonged.

According to an aspect of the present application, a controller is configured to selectively implement a normal control, which is to apply a first voltage to a first electrode, which is in a measurement chamber, and a second electrode, which is in a reference gas chamber, of the first cell in order to remove oxygen in gas to be detected in the measurement chamber, and a reduction control, which is to apply a second voltage higher than the first voltage to the first electrode and the second electrode in order to reduce a third electrode that is in the measurement chamber and is oxidized. The controller is configured to determine whether implementation of the reduction control is necessary and to prohibit implementation of the reduction control on determination that implementation of the reduction control is not necessary.

This configuration prohibits implementation of the reduction control in a state where the implementation of the reduction control is not necessary, thereby to enable to avoid unnecessary implementation of the reduction control. In this way, the configuration enables to avoid a delay in activation of the gas sensor resulting from implementation of the unnecessary reduction control. Therefore, the configuration enables to accelerate the activation of the gas sensor.

Hereinafter, embodiments of a gas sensor will be described with reference to drawings. To facilitate understanding, identical constituent elements are designated with identical symbols in the drawings where possible, and the duplicate description thereof is omitted.

First Embodiment

First, an outline of an exhaust gas purification system for a vehicle will be described. The exhaust gas purification system is equipped with a gas sensor according to a first embodiment.

As shown in FIG. 1, an exhaust purification system 1 for a vehicle according to the present embodiment is configured to purify exhaust gas discharged from an engine 10. The engine 10 is a diesel engine. An exhaust pipe 11 that forms an exhaust passage is connected to the engine 10. The exhaust pipe 11 is equipped with an oxidation catalytic converter 12 and a selective catalytic reduction converter (hereinafter referred to as SCR catalytic converter) 13 that are sequentially connected from the side of the engine 10. The oxidation catalytic converter 12 includes a diesel oxidation catalyst 14 and a diesel particulate filter (DPF) 15. The SCR catalytic converter 13 includes an SCR catalyst 16 that is a selective reduction-type catalyst. A urea water addition valve 17 is provided between the oxidation catalytic converter 12 and the SCR catalytic converter 13 in the exhaust pipe 11 to add and supply urea water (urea aqueous solution) as a reducing agent into the exhaust pipe 11.

The diesel oxidation catalyst 14 of the oxidation catalytic converter 12 mainly includes a ceramic support, an oxide mixture containing aluminum oxide, cerium dioxide and/or zirconium dioxide as components, and a noble metal catalyst such as platinum, palladium and/or rhodium. The diesel oxidation catalyst 14 oxidizes and purifies hydrocarbons, carbon monoxides, nitrogen oxides and the like contained in the exhaust gas. The diesel oxidation catalyst 14 raises the exhaust gas temperature by using heat generated during the catalytic reaction.

The DPF 15 is formed of honeycomb structures that supports platinum group catalysts such as platinum and palladium on its porous ceramics. The DPF 15 causes the particulate matter contained in the exhaust depositing gas to be deposited on partition walls of the honeycomb structure thereby to collect the particulate matter. The deposited particulate matter is subjected to combustion to be oxidized and purified. This combustion is implemented by utilizing increase in temperature of the diesel oxidation catalyst 14 and decrease in combustion temperature of the particulate matter caused by an additive.

The SCR catalytic converter 13 is a post-treatment device of the oxidation catalytic converter 12 and is configured to reduce NOx into nitrogen and water. The SCR catalyst 16 includes a substrate such as zeolite or alumina that carries a noble metal such as Pt on the surface of the substrate. The SCR catalyst 16 is added with urea as a reducing agent when the catalyst temperature is in the active temperature range thereby to reduce and purify NOx.

Gas sensors 21 to 23 are placed in the exhaust pipe 11. The gas sensor 21 is placed upstream of the oxidation catalytic converter 12. The gas sensor 22 is placed upstream of the urea water addition valve 17 and is placed between the oxidation catalytic converter 12 and the SCR catalytic converter 13. The gas sensor 23 is placed downstream of the SCR catalytic converter 13. The gas sensors 21 to 23 detect the respective NOx concentration in the exhaust gas at the respective detection positions. The positions and the numbers of gas sensors in the engine exhaust system may be arbitrary determined. In the present embodiment, the exhaust gas corresponds to detected gas, and NOx in the exhaust gas corresponds to a specific gas component.

Sensor controllers (SCUs) 31 to 33 are connected to the gas sensors 21 to 23, respectively, and receives detection signals of the gas sensors 21 to 23, respectively. The SCUs 31 to 33 are electronic control devices each including a microcomputer including a CPU and various memory devices and peripheral circuits thereof. Each of the SCUs 31 to 33 computes the oxygen concentration in the exhaust gas, the NOx concentration as the concentration of the specific gas component, and the like based on the respective one of the detection signals (limit current signals) of the gas sensors 21 to 23.

The SCUs 31 to 33 are connected to a communication line 34 such as a CAN bus and are connected to various ECUs (for example, an engine ECU 35) via the communication line 34. That is, the SCUs 31 to 33 and the engine ECU 35 are configured to exchange information with each other by using the communication line 34. For example, the SCUs 31 to 33 transmits information on the oxygen concentration and NOx concentration of the exhaust gas to the engine ECU 35. The engine ECU 35 is an electronic controller that includes a microcomputer having a CPU and various memory devices and its peripheral circuits and controls the engine 10 and various exhaust system devices. The engine ECU 35 performs a fuel injection control and the like based on, for example, an accelerator position and an engine rotation speed. Further, the engine ECU 35 implements an idling stop control to temporarily stop the engine 10.

Further, the engine ECU 35 controls addition of the urea water by manipulating the urea water addition valve 17 based on the NOx concentrations detected by using the gas sensors 21 to 23, respectively. The control of addition of urea water will be briefly described as follows. The engine ECU 35 computes a urea water addition amount based on the NOx concentration detected by using the gas sensors 21 and 22 on the upstream side of the SCR catalytic converter 13. The engine ECU 35 implements feedback-correction on the urea water addition amount such that the NOx concentration detected by using the gas sensor 23 on the downstream side of the SCR catalytic converter 13 becomes as small as possible. The engine ECU 35 controls the operation of the urea water addition valve 17 based on the urea water addition amount.

Figure 2:
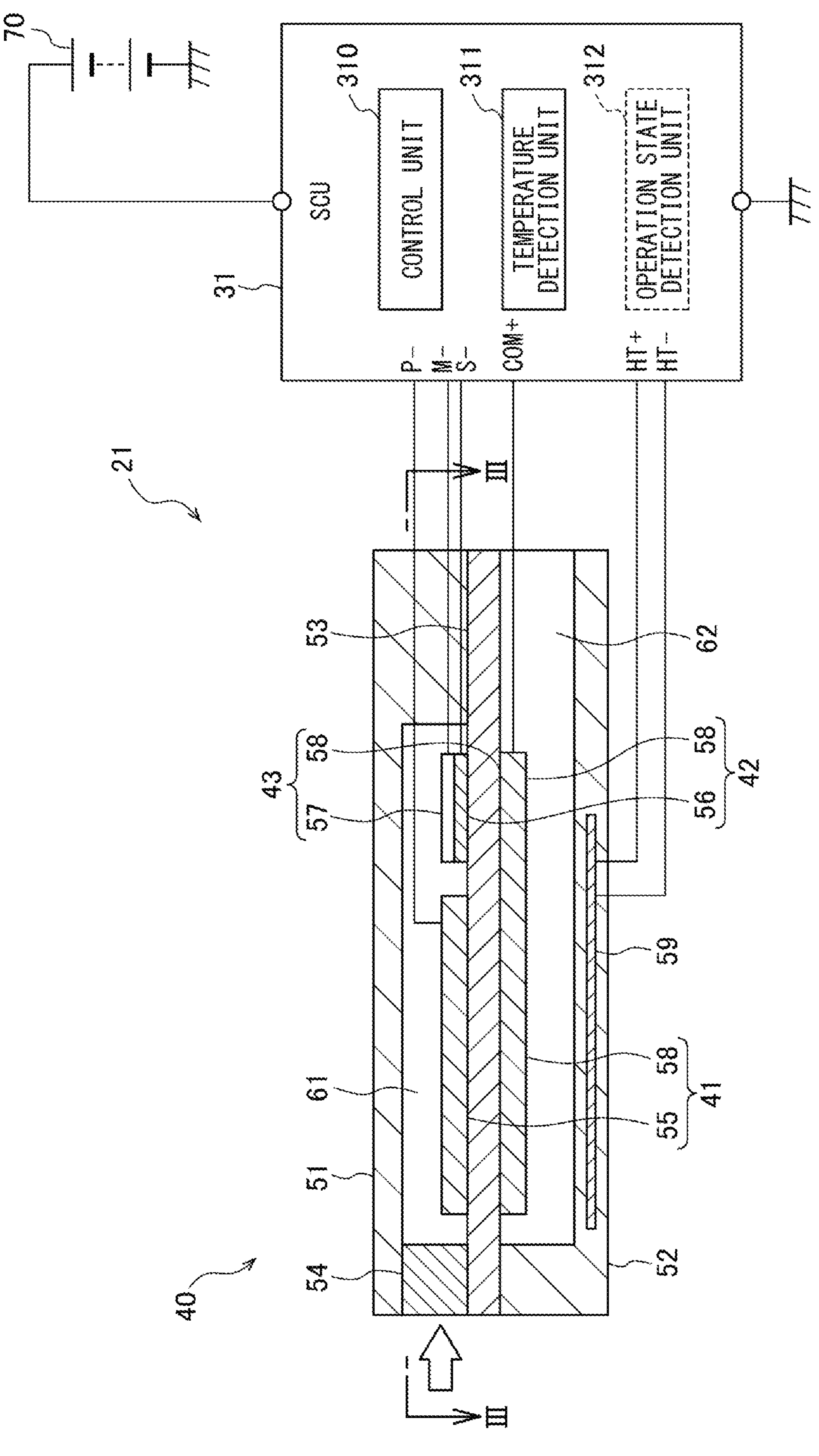
FIG. 2 is a block diagram showing a schematic configuration of a gas sensor according to a first embodiment.
Figure 3:
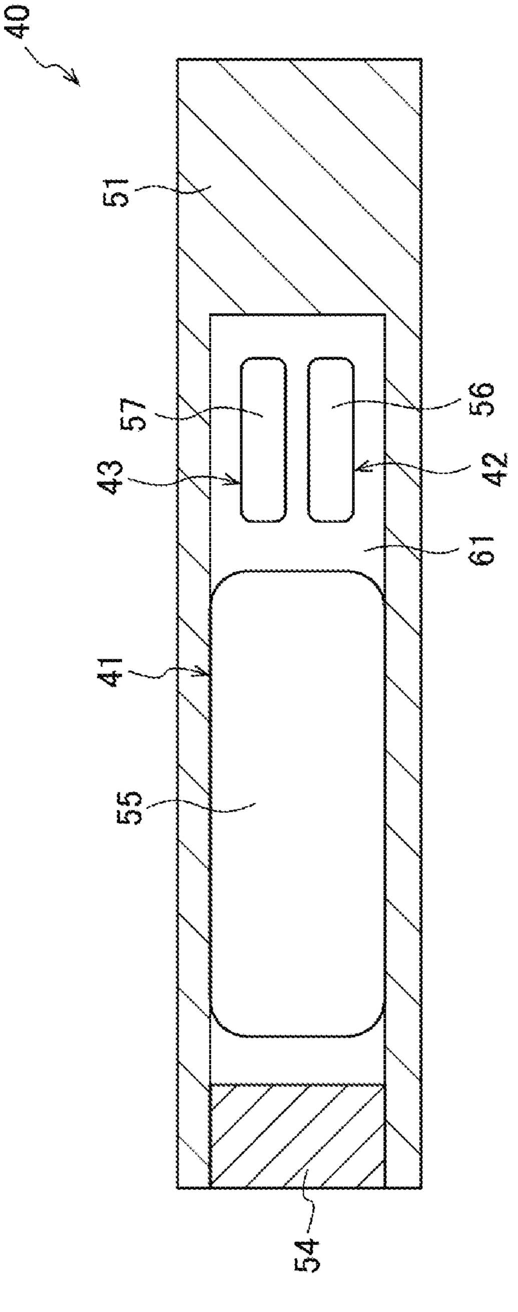
FIG. 3 is a cross-sectional view showing a cross-section taken along a line III-III in FIG. 2.

Subsequently, the configuration of the gas sensors 21 to 23 will be described. All the gas sensors 21 to 23 have the same structure. All the SCUs 31 to 33 have the same structure. Therefore, the structure of the gas sensor 21 and the structure of the SCU 31 will be described below as representative examples. FIGS. 2 and 3 are diagrams each showing an internal structure of a sensor element 40 of the gas sensor 21. In the drawings, the left-right direction is a longitudinal direction of the sensor element 40, and the left side is an front end side of the sensor element 40. The sensor element 40 has a three-cell structure including a pump cell 41, a sensor cell 42, and a monitor cell 43. The monitor cell 43 has a function to discharge oxygen in the gas similarly to the pump cell 41 and may be referred to as an auxiliary pump cell or a second pump cell.

The sensor element 40 includes the pump cell 41, the sensor cell 42, the monitor cell 43, a first main body 51, a second main body 52, a solid electrolyte body 53, a diffusion resistor 54, and a heater 59. The first main body 51 and the second main body 52 are arranged so as to interpose the solid electrolyte body 53 in the thickness direction with predetermined gaps therebetween. A gap formed between the first main body 51 and the solid electrolyte body 53 defines a measurement gas chamber 61. One side surface of the first main body 51 is open. The diffusion resistor 54 is placed on the open side surface. The measurement gas chamber 61 introduces exhaust gas that flows through the exhaust pipe 11 thereinto through the diffusion resistor 54. The diffusion resistor 54 is made of a porous material such as alumina or a material having pores. The diffusion resistor 54 is provided to limit an amount of exhaust gas to be drawn into the measurement gas chamber 61. The other gap formed between the second main body 52 and the solid electrolyte body 53 defines a reference gas chamber 62. The reference gas chamber 62 introduces atmospheric air that is a reference oxygen concentration gas.

The pump cell 41 is placed at a position closer to the diffusion resistor 54 than the sensor cell 42 and the monitor cell 43. The pump cell 41 removes oxygen in the exhaust gas that is drawn from the diffusion resistor 54. In the present embodiment, the pump cell 41 corresponds to a first cell. The pump cell 41 includes the solid electrolyte body 53, a pump electrode 55, and the common electrode 58. The pump electrode 55 is placed on the surface of the solid electrolyte body 53 on the side of the measurement gas chamber 61. The common electrode 58 is placed on the surface of the solid electrolyte body 53 on the side of the reference gas chamber 62. The pump electrode 55 is formed of a NOx inert electrode that is configured to hardly decompose NOx, such as, an electrode formed of a Pt—Au (platinum-gold) alloy. The common electrode 58 is placed so as to extend to a region corresponding to the sensor cell 42 and the pump cell 41. A pump voltage Vp is applied between the pump electrode 55 and the common electrode 58. In the present embodiment, the pump cell 41 corresponds to a first cell, the pump electrode 55 corresponds to a first electrode, and the common electrode 58 corresponds to a second electrode.

The exhaust gas drawn into the measurement gas chamber 61 through the diffusion resistor 54 is brought into contact with the pump electrode 55. When oxygen in the exhaust gas comes into contact with the pump electrode 55, oxygen ions are generated on the pump electrode 55. The oxygen ions flow inside the solid electrolyte body 53 toward the common electrode 58 and discharge electric charges on the common electrode 58 to become oxygen. This oxygen is released from the reference gas chamber 62 to the atmosphere. A pump current Ip flows between the pump electrode 55 and the common electrode 58 in accordance with the flow of the electric charges at this time. Therefore, the pump current Ip shows a value corresponding to the amount of oxygen removed on the pump cell 41. In other words, the pump current Ip shows the oxygen concentration in the exhaust gas.

As shown in FIG. 3, the sensor cell 42 is placed at a position farther from the diffusion resistor 54 than the pump cell 41. The sensor cell 42 detects the concentration of NOx and residual oxygen in the exhaust gas that has passed through the pump cell 41. In the present embodiment, the sensor cell 42 corresponds to the second cell.

As shown in FIG. 2, the sensor cell 42 includes the solid electrolyte body 53, a sensor electrode 56, and the common electrode 58. The sensor electrode 56 is placed on the surface of the solid electrolyte body 53 on the side of the measurement gas chamber 61. The sensor electrode 56 is a NOx active electrode that is excellent in decomposing of NOx, for example, an electrode formed of a Pt—Rh (platinum-rhodium) alloy. A sensor voltage Vs is applied between the sensor electrode 56 and the common electrode 58. In the present embodiment, the sensor cell 42 corresponds to a second cell, the sensor electrode 56 corresponds to a third electrode, and the common electrode 58 corresponds to a fourth electrode.

The exhaust gas that has passed through the pump electrode 55, that is, the exhaust gas from which oxygen has been removed, is brought into contact with the sensor electrode 56. When NOx in the exhaust gas comes into contact with the sensor electrode 56, NOx is decomposed into nitrogen and oxygen on the sensor electrode 56. In addition, when residual oxygen that has not been removed by the pump electrode 55 is present in the exhaust gas, the residual oxygen is also brought into contact with the sensor electrode 56. Oxygen decomposed on the sensor electrode and residual oxygen in the exhaust gas come into contact with the sensor electrode 56, thereby oxygen ions are generated on the sensor electrode 56. The oxygen ions flow inside the solid electrolyte body 53 toward the common electrode 58 and discharge electric charges on the common electrode 58 to become oxygen. This oxygen is released from the reference gas chamber 62 to the atmosphere. A sensor current Is flows between the sensor electrode 56 and the common electrode 58 in accordance with the flow of the electric charges at this time. Therefore, the sensor current Is indicates a value corresponding to the NOx concentration and residual oxygen concentration in the exhaust gas.

As shown in FIG. 3, the monitor cell 43 is arranged so as to be aligned with the sensor cell 42. The monitor cell 43 detects the concentration of residual oxygen in the exhaust gas that has passed through the pump cell 41. As shown in FIG. 2, the monitor cell 43 includes a solid electrolyte body 53, a monitor electrode 57, and the common electrode 58. The monitor electrode 57 is placed on the surface of the solid electrolyte body 53 on the side of the measurement gas chamber 61. More specifically, the monitor electrode 57 is placed on the surface of the sensor electrode 56 on the opposite side to the solid electrolyte body 53. The monitor electrode 57 is formed of a NOx inert electrode that is configured to hardly decompose NOx, such as, an electrode formed of a Pt—Au (platinum-gold) alloy. A monitor voltage Vm is applied between the monitor electrode 57 and the common electrode 58. In the present embodiment, the monitor cell 43 corresponds to a third cell, the monitor electrode 57 corresponds to a fifth electrode, and the common electrode 58 corresponds to a sixth electrode.

The exhaust gas from which oxygen has been removed by the pump electrode 55 is brought into contact with the monitor electrode 57. In a case where residual oxygen is present in the exhaust gas, the residual oxygen is brought into contact with the monitor electrode 57, and therefore oxygen ions are generated on the monitor electrode 57. The oxygen ions flow inside the solid electrolyte body 53 toward the common electrode 58 and discharge electric charges on the common electrode 58 to become oxygen. This oxygen is released from the reference gas chamber 62 to the atmosphere. A monitor current Im flows between the monitor electrode 57 and the common electrode 58 in accordance with the flow of the electric charges at this time. Therefore, the monitor current Im shows a value corresponding to the concentration of residual oxygen in the exhaust gas.

As shown in FIG. 2, the pump electrode 55 of the pump cell 41, the sensor electrode 56 of the sensor cell 42, and the monitor electrode 57 of the monitor cell 43 are provided in the same measurement gas chamber 61. The heater 59 is provided inside the second main body 52. The heater 59 generates heat in accordance with energization thereof to heat the solid electrolyte body 53 and to maintain the temperature of the solid electrolyte body 53 at an activation temperature.

The SCU 31 detects the pump current Ip sent from the pump cell 41, the sensor current Is sent from the sensor cell 42, and the monitor current Im sent from the monitor cell 43. The SCU 31 implements various arithmetic processes based on the current values Ip, Is, and Im and implements a drive control of the heater 59 and the like. Specifically, the pump current detection value Ip detected by the SCU 31 has a correlation with the oxygen concentration in the exhaust gas. The sensor current detection value Is detected by using the SCU 31 has a correlation with the NOx concentration and the residual oxygen in the exhaust gas. A monitor current detection value Im detected by the SCU 31 has a correlation with the residual oxygen in the exhaust gas. The SCU 31 computes an oxygen concentration detection value based on the pump current detection value Ip and by using those values. Further, the SCU 31 subtracts the monitor current detection value Im from the sensor current detection value Is and computes a NOx concentration detection value based on the subtraction value. The SCU 31 transmits the computed oxygen concentration detection value and NOx concentration detection value to the engine ECU 35 shown in FIG. 1.

The SCU 31 includes a controller 310 that controls the pump cell 41 and a temperature detector 311 that detects the temperature of the sensor element 40. The controller 310 changes the pump voltage Vp thereby to selectively implement a normal control for removing oxygen in the exhaust gas and a reduction control for reducing the sensor electrode 56 that has been oxidized.

Specifically, the controller 310 implements the normal control for controlling the pump voltage Vp at the normal voltage V10 when detecting the NOx concentration. The normal voltage V10 is set such that the oxygen concentration in the measurement gas chamber 61 is equal to or lower than a predetermined concentration. More specifically, the normal voltage V10 is within a voltage range in which the solid electrolyte body 53 exhibits a limit current characteristic in which the pump current Ip flowing through the pump cell 41 hardly changes even when the voltage applied to the pump cell 41 changes. For example, the normal voltage V10 is within a range of $0.3\ V \leq V10 \leq 0.4\ V$. In the present embodiment, the normal voltage V10 corresponds to a first voltage.

On the other hand, in a state where the gas sensor 21 is not used, such as a state where the engine 10 is stopped, the sensor electrode 56 may be oxidized. In a state where the sensor electrode 56 is oxidized, the sensor current Is that is output from the sensor cell 42 may vary during a period after the gas sensor 21 is started until the oxygen stored in the sensor electrode 56 is removed. This causes an error in the NOx concentration detected by the SCU 31.

In consideration of that, when removing oxygen stored in the sensor electrode 56, the controller 310 implements a reduction control for controlling the pump voltage Vp at a removal voltage V20 that is higher than the normal voltage V10. The removal voltage V20 is set in a range of, for example, $0.5\ V \leq V20 \leq 2.0\ V$. The controller 310 sets the pump voltage Vp at the removal voltage V20, thereby to cause the water present in the measurement gas chamber 61 to be decomposed to generate hydrogen as a reducing gas. The hydrogen as generated adheres to the sensor electrode 56, thereby to enable to remove the oxygen occluded in the sensor electrode 56 quickly. In this way, the configuration enables to shorten the activation time of the gas sensor 21. In the present embodiment, the removal voltage V20 corresponds to a second voltage.

Figure 4:
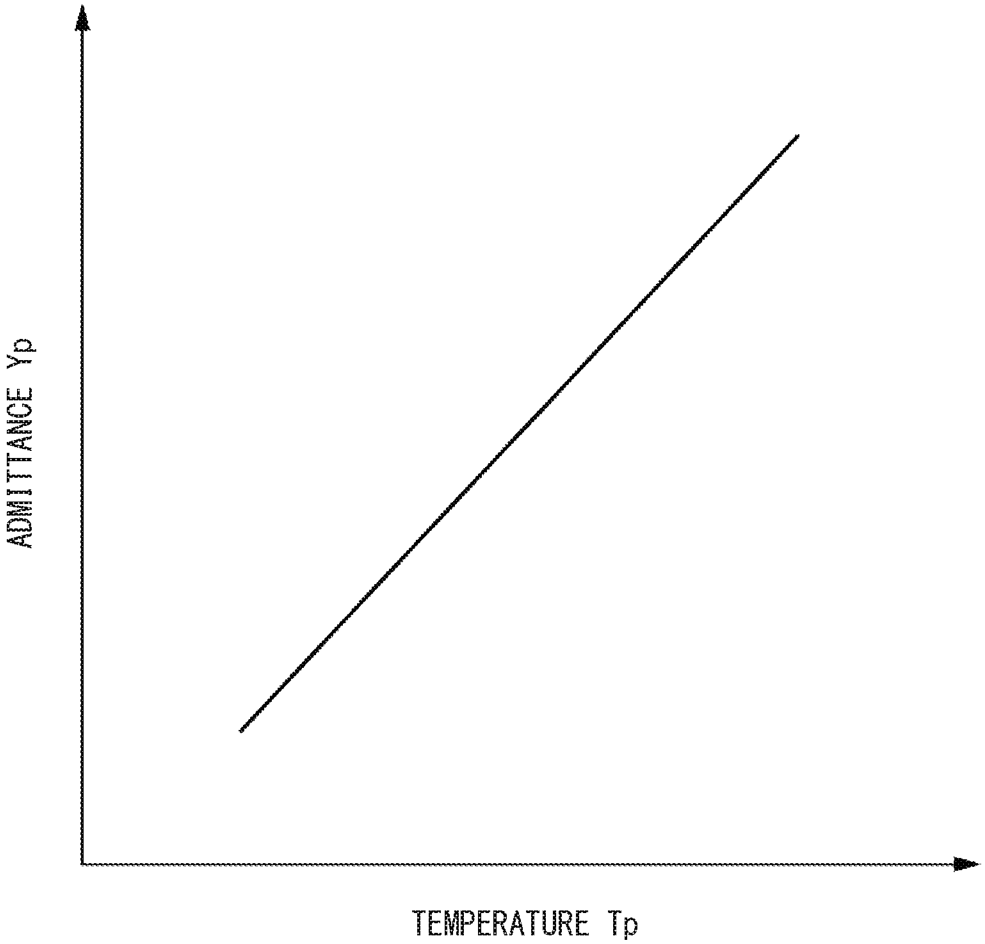
FIG. 4 is a graph showing a relationship between an admittance and a temperature of the pump cell according to the first embodiment.

The temperature detector 311 detects a temperature Tp of the pump cell 41 as a temperature of the sensor element 40. Specifically, the temperature Tp of the pump cell 41 and the admittance Yp have a correlation as shown in FIG. 4 therebetween. The temperature detector 311 detects the pump current Ip when an AC voltage is applied to the electrodes 55 and 58 of the pump cell 41. The temperature detector 311 computes the admittance Yp of the pump cell 41 based on the detected pump current Ip and the applied AC voltage by using an arithmetic expression or the like. The temperature detector 311 computes the temperature Tp of the pump cell 41 by using the admittance Yp as computed with reference to the map shown by FIG. 4. In the present embodiment, the temperature Tp of the pump cell 41 corresponds to an element temperature parameter.

It is noted that, in the configuration to implement the reduction control when the operation of the gas sensor 21 is started, the following concerns arise. As shown in FIG. 2, the SCU 31 is driven by using the electric power supplied from a battery 70 mounted on the vehicle. In the configuration, the time point at which the gas sensor 21 starts its operation generally coincides with the time point at which the battery 70 starts power supply to the SCU 31.

Figure 5:
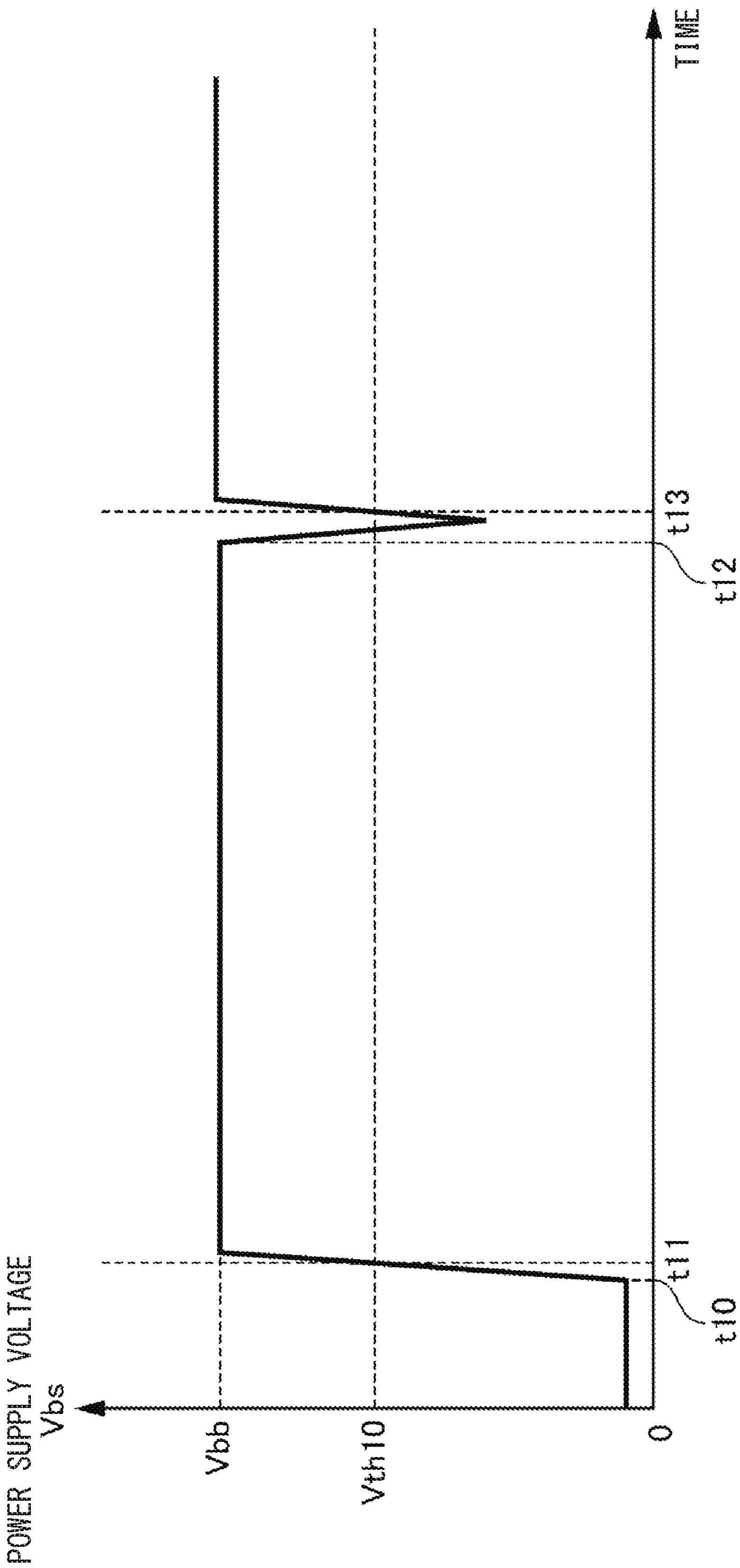
FIG. 5 is a time chart showing a transition of a power supply voltage of an SCU according to the first embodiment.

Specifically, as shown in FIG. 5, it is assumed that the vehicle is started at, for example, time t10. In this case, the power supply voltage Vbs supplied from the battery 70 to the gas sensor 21 increases to a predetermined battery voltage Vbb after the time t10. When, at time t11, the power supply voltage Vbs reaches the voltage threshold Vth10, which is set to a value smaller than the predetermined battery voltage Vbb, the SCU 31 starts its operation. Therefore, the SCU 31 implements the reduction control at time t11.

In addition, it is further assumed that the engine ECU 35 implements the idling stop control after the engine 10 is warmed up, and the engine ECU 35 restarts the engine 10 at time t12. In such a case, the power supply voltage Vbs may drop once unintentionally, and thereafter, the power supply voltage Vbs may recover to increase to the predetermined battery voltage Vbb after a few milliseconds subsequent to the drop in the power supply voltage Vbs. In this case, after the power supply voltage Vbs once drops below the voltage threshold Vth10 and then recovers to reach the voltage threshold Vth10 at time t13, the SCU 31 may erroneously determine that the operation of the gas sensor 21 is started and may implement the reduction control. It is further noted that, in such a state, the sensor electrode 56 has not been oxidized. Therefore, the reduction control causes the pump cell 41 to generate the hydrogen, and the hydrogen as generated could rather disable the sensor cell 42 for proper detection of NOx in the exhaust gas.

In consideration of that, the controller 310 according to the present embodiment determines whether the implementation of the reduction control is necessary and prohibits the implementation of the reduction control on determination that the implementation of the reduction control is not necessary. Hereinafter, a state, in which the engine ECU 35 implements the idling stop control and restarts the engine 10 after the engine 10 is warmed up, is referred to as an after-warm-up restart of the engine 10.

Subsequently, a specific procedure of the processing to determine whether to implement or prohibit the reduction control of the SCU 31 will be described with reference to FIG. 6. The controller 310 repeatedly executes the processing shown in FIG. 6 at a predetermined computation cycle.

Figure 6:
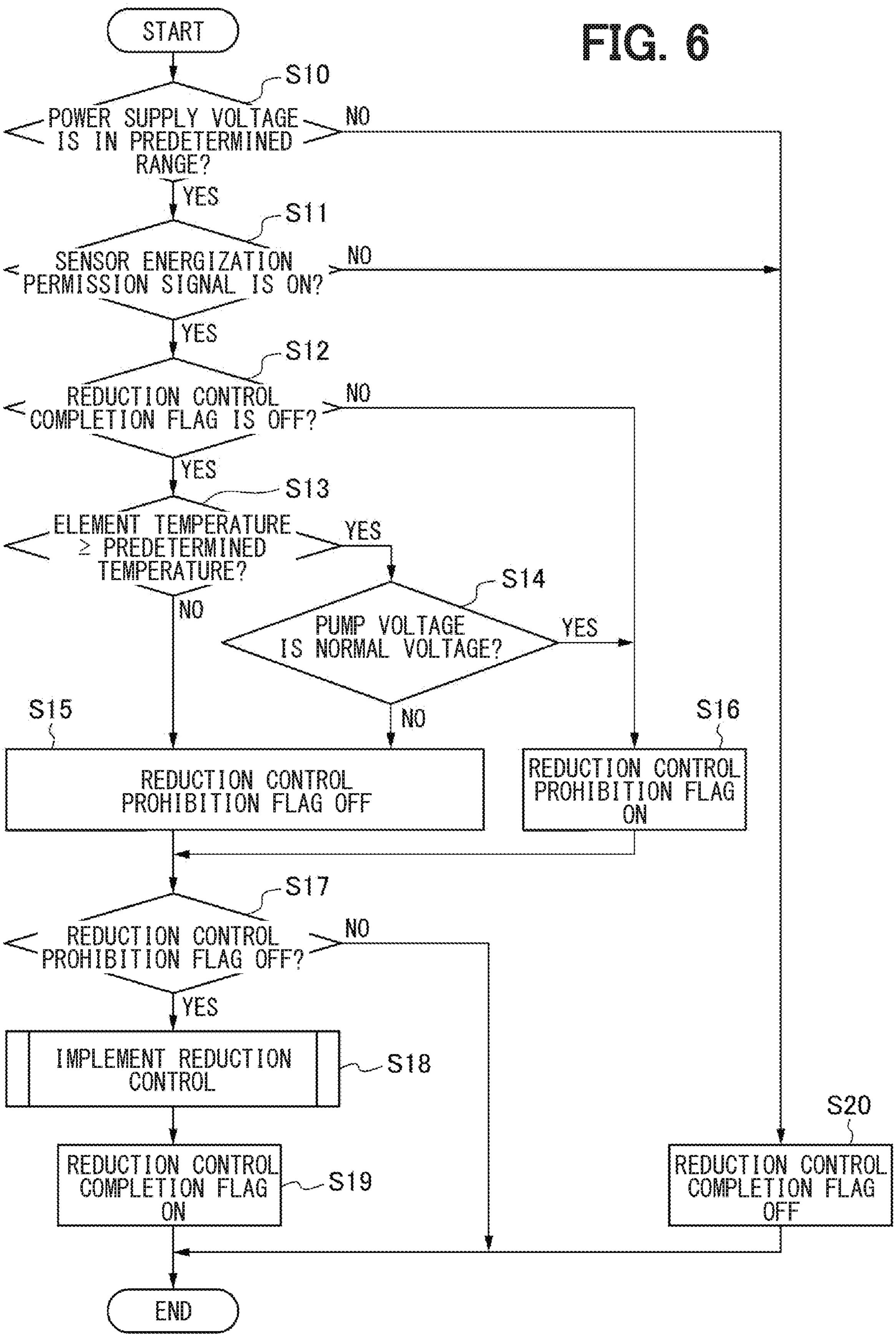
FIG. 6 is a flowchart showing a procedure of processing implemented by the SCU according to the first embodiment.

As shown in FIG. 6, at step S10, the controller 310 first determines whether the power supply voltage Vbs is within a predetermined range. For example, in a configuration in which the predetermined battery voltage Vbb is 12 V, the controller 310 determines in the process of step S10 whether the power supply voltage Vbs satisfies a condition of 9 V≤Vbs≤18 V. The power supply voltage Vbs applied to the SCU 31 is less than 9 V in the state before the engine 10 is started. Therefore, the controller 310 makes a negative determination in the process of step S10. In this case, the controller 310 sets a reduction control completion flag F10 to the off state in the process of step S20.

To the contrary, in response to start of the engine 10, the battery 70 applies the voltage to the SCU 31. Therefore, the power supply voltage Vbs of the SCU 31 satisfies the condition of 9 V≤Vbs≤18 V. In this case, the controller 310 makes an affirmative determination in the process of step S10. Subsequently, the controller 310 determines as a subsequent process of step S11 whether a sensor energization permission signal is in the on state. The sensor energization permission signal is a signal sent from the engine ECU 35 to the SCU 31. For example, when the engine ECU 35 determines that the exhaust pipe 11 is dry, the engine ECU 35 sets the sensor energization permission signal to the on state. The engine ECU 35 determines that the exhaust pipe 11 is dry on elapse of a predetermined time from the start of the engine 10 or on increase in the temperature of the exhaust gas flowing through the exhaust pipe 11 to be a predetermined temperature or higher. When the sensor energization permission signal is not in the on state, the controller 310 makes a negative determination in step S11 and sets the reduction control completion flag F10 to the off state in the process of step S20.

When the sensor energization permission signal is turned on after the engine 10 is started, the controller 310 makes an affirmative determination in the process of step S11. As the subsequent process in step S12, the controller 310 determines whether the reduction control completion flag F10 is in the off state. When the reduction control completion flag F10 is in the off state, the controller 310 makes an affirmative determination in the process of step S12. Subsequently, the controller 310 determines whether the element temperature is equal to or higher than a predetermined temperature in the process of step S13.

Specifically, in step S13, the controller 310 determines whether the temperature Tp of the pump cell 41 detected with the temperature detector 311 is equal to or higher than a predetermined temperature Tpth. The pump cell 41 exhibits its oxygen removal function at a temperature of about, for example, 770° C. The pump cell 41 is capable of exhausting oxygen in the measurement gas chamber 61 also at this temperature. The predetermined temperature Tpth is set to a temperature that is the same as or higher than the temperature at which the pump cell 41 exhibits the oxygen removal function. In the present embodiment, the process of step S13 corresponds to a process to determine whether the element temperature parameter is equal to or greater than a predetermined value.

For example, when the engine 10 implements cold start, the temperature Tp of the pump cell 41 may be lower than the predetermined temperature Tpth. Therefore, in such a state, the controller 310 makes a negative determination in the process of step S13 and sets the reduction control prohibition flag F20 to the off state in the subsequent process of step S15.

The controller 310 determines whether the reduction control prohibition flag F20 is set to the off state in the process of step S17 that is subsequent to step S15. When the reduction control prohibition flag F20 is set to the OFF state, the controller 310 makes an affirmative determination in the process of step S17 and executes the reduction control in the subsequent process of step S18. In addition, in the process of step S19 subsequent to step S18, the controller 310 sets the reduction control completion flag F10 to the on state and subsequently ends the series of processes.

Thereafter, when the controller 310 executes the process shown in FIG. 6, the controller 310 makes a negative determination in the process of step S12 because the reduction control completion flag F10 is set to the on state. In this case, the controller 310 sets the reduction control prohibition flag F20 to the on state as the process of step S16. In this way, the controller 310 makes a negative determination in the process of step S17. That is, the controller 310 avoids implementation of the reduction control. In this case, the gas sensor 21 is in a normal use state to detect the oxygen concentration and the NOx concentration.

To the contrary, it is assumed that the power supply voltage Vbs of the SCU 31 temporarily drops below 9 V when the engine 10 is restarted after being warmed up. In this case, the controller 310 makes a negative determination in the process of step S10 and sets the reduction control completion flag F10 to the off state.

Thereafter, when the controller 310 executes the process shown in FIG. 6, the reduction control completion flag F10 is set to the off state, and therefore, the controller 310 makes an affirmative determination in the process of step S12. At this time, the engine 10 is in a warm-up state, and therefore, the temperature Tp of the pump cell 41 is equal to or higher than the predetermined temperature Tpth. Therefore, the controller 310 makes an affirmative determination in the process of step S13. In this case, the controller 310 determines whether the pump voltage Vp is the normal voltage V10 in the process of step S14. In the present embodiment, the process of step S14 corresponds to a process to determine whether to implement the normal control.

When the controller 310 makes an affirmative determination in step S14, that is, when the pump voltage Vp is the normal voltage V10, the controller 310 determines that the normal control is being performed. Therefore, the controller 310 maintains the reduction control prohibition flag F20 in the on state in the process of step S16. In this case, the controller 310 makes a negative determination in the process of step S17. Therefore, the controller 310 avoids implementation of the reduction control. The state in which the controller 310 makes an affirmative determination in step S13 and makes an affirmative determination in step S14 is a state where the temperature Tp of the pump cell 41 is equal to or higher than the predetermined temperature Tpth and the pump voltage Vp is set to the normal voltage V10. In such a condition, the pump cell 41 exhibits the oxygen removal function, and therefore, the sensor electrode 56 is not oxidized. That is, the reduction control need not be implemented. Therefore, the reduction control prohibition flag F20 is maintained in the ON state.

To the contrary, in a case where the engine 10 is restarted after warming up and where the temperature Tp of the pump cell 41 is lower than the predetermined temperature Tpth, the oxygen removal function in the pump cell 41 is low. Therefore, the sensor electrode 56 may be oxidized. In this case, the controller 310 makes a negative determination in the process of step S13 and sets the reduction control prohibition flag F20 to the off state in the subsequent process of step S15. In this way, the controller 310 makes an affirmative determination in the process of step S17. Therefore, the controller 310 is permitted to implement the reduction control in the process of step S18 thereby to reduce the sensor electrode 56.

Further, in a case where the engine 10 is restarted after the warming up and where the pump voltage Vp is not set to the normal voltage V10, the oxygen removing function in the pump cell 41 is insufficient. Therefore, the sensor electrode 56 may be oxidized. In this case, the controller 310 makes a negative determination in the process of step S14 and sets the reduction control prohibition flag F20 to the off state in the subsequent process of step S15. In this way, the controller 310 makes an affirmative determination in the process of step S17. Therefore, the controller 310 is permitted to implement the reduction control in the process of step S18 thereby to reduce the sensor electrode 56.

Subsequently, an example of the operation of the gas sensor 21 of the present embodiment will be described.

Figure 7:
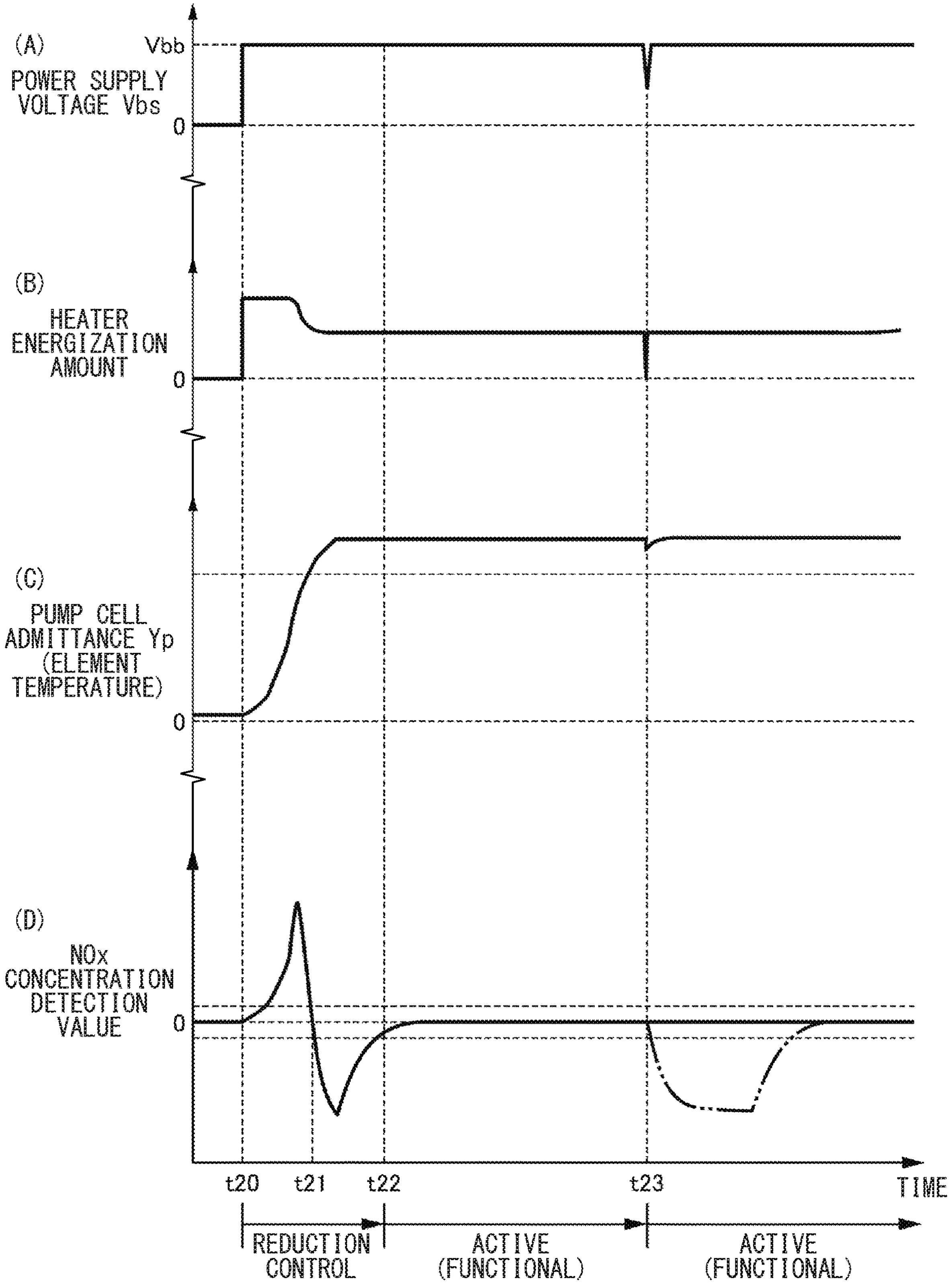
FIG. 7 is a view including time charts (A) to (D) showing respective transitions of the power supply voltage of the SCU, a current amount of a heater, an admittance of a pump cell, and a NOx concentration detection value according to the first embodiment.

As shown in the time chart (A) in FIG. 7, assuming that the engine 10 is cold-started at, for example, the time t20, the power supply voltage Vbs of the SCU 31 rises to the battery voltage Vbb. Accordingly, as shown in the time chart (B) in FIG. 7, the energization amount of the heater 59 increases at the time t20, and the heater 59 therefore generates heat. Thus, subsequent to the time t20, the temperature of each of the cells 41 to 43 rises. Therefore, as shown in the time chart (C) in FIG. 7, the admittance Yp of the pump cell 41 also increases subsequent to the time t20.

When the engine 10 is started at the time t20, the controller 310 implements the reduction control. Immediately after the time t20, oxygen is occluded in the sensor electrode 56. Therefore, as shown in the time chart (D) in FIG. 7, the NOx density detection value rises in the period from the time t20 to the time t21 due to the oxidization of the sensor electrode 56. Subsequently, after the time 21, the sensor electrode 56 is rapidly reduced by hydrogen generated by the pump cell 41, so that the NOx concentration detection value once decreases and then becomes stable after the time t22.

On the other hand, as shown in the time chart (A) in FIG. 7, assuming that the engine 10 is restarted after warming up at the time t23, the power supply voltage Vbs of the SCU 31 temporarily decreases. Accordingly, as shown in the time charts (B) and (C) in FIG. 7, the energization amount of the heater 59 and the admittance Yp of the pump cell 41 are also temporarily reduced.

At this time, assuming that the SCU 31 implements the reduction control after restarting, the sensor electrode 56 is reduced. In this state, the NOx concentration in the actual exhaust gas has not changed. Nevertheless, even in this state, as shown by the two-dot chain line in the time chart (D) in FIG. 7, the NOx concentration detection value varies to decrease.

To the contrary, the gas sensor 21 according to the present embodiment does not implement the reduction control in the state where the power supply voltage Vbs of the SCU 31 temporarily decreases. Therefore, as shown by the solid line in the time chart (D) in FIG. 7, variation in the NOx concentration detection value can be suppressed. Therefore, the configuration enables to detect the NOx concentration with higher accuracy.

The gas sensor 21 according to the present embodiment described above enables to produce the operations and effects shown in the following clauses (1) to (3).

(1) The configuration prohibits the implementation of the reduction control in the state where implementation of the reduction control is not necessary. Therefore, the configuration enables to avoid implementation of the reduction control when the implementation is not necessary. In this way, the configuration enables to avoid a delay in activation of the gas sensor 21 that results from implementation of the unnecessary reduction control. Therefore, the configuration enables to accelerate the activation of the gas sensor 21.

(2) The controller 310 determines whether the pump cell 41 exhibits the oxygen removal function in the determination process of step S13 and step S14 shown in FIG. 6. In a case where step S13 makes an affirmative determination and where step S14 makes an affirmative determination, the controller 310 determines that the pump cell 41 exhibits the oxygen removal function. Therefore, the controller 310 determines that the reduction control need not be implemented and sets the reduction control prohibition flag F20 to the on state in step S16. This configuration enables to avoid implementation of the reduction control in a state where the sensor electrode 56 is not oxidized and therefore enables to avoid implementation of the unnecessary reduction control.

(3) The temperature detector 311 acquires the temperature Tp of the pump cell 41 based on the admittance Yp of the pump cell 41 when the AC voltage is applied to the electrodes 55 and 58 of the pump cell 41. This configuration enables to detect the temperature Tp of the pump cell 41 with a simple configuration.

(Modifications)

Subsequently, a modified example of the gas sensor of the first embodiment will be described.

Figure 8:
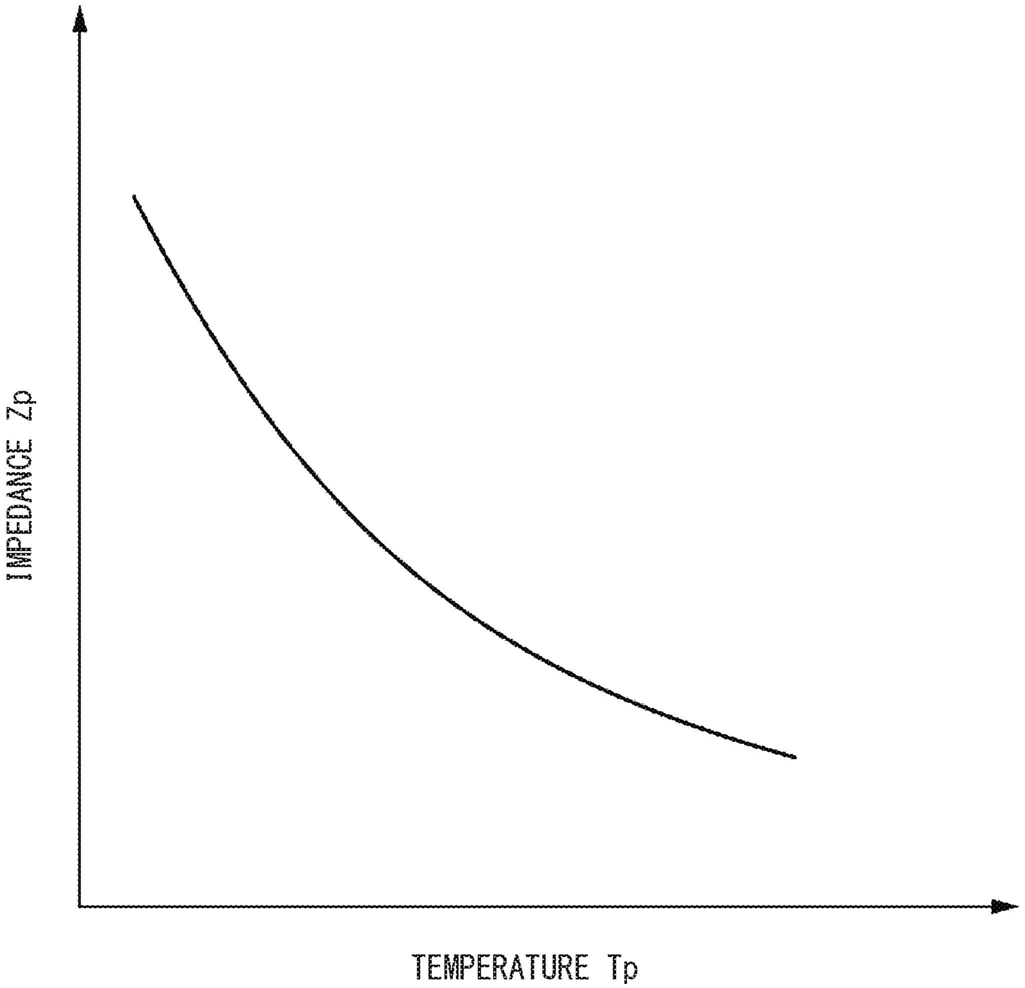
FIG. 8 is a graph showing a relationship between an impedance and a temperature of the pump cell according to a modification of the first embodiment.

The temperature detector 311 may use the impedance Zp of the pump cell 41 in order to detect the temperature Tp of the pump cell 41. Specifically, as shown in FIG. 8, the temperature Tp of the pump cell 41 and the impedance Zp have a correlation therebetween. The controller 310 detects the pump current Ip, which flows when the AC voltage is applied to the electrodes 55 and 58 of the pump cell 41. The controller 310 computes the impedance Zp of the pump cell 41 based on the detected pump current Ip and the applied AC voltage by using an arithmetic formula. The controller 310 further computes the temperature Tp of the pump cell 41 from the computed impedance Zp with reference to the map shown in FIG. 8.

Second Embodiment

Subsequently, a second embodiment of the gas sensor 21 will be described. Hereinafter, a difference from the gas sensor 21 of the first embodiment will be mainly described.

The controller 310 of the first embodiment executes the processing of steps S13 and S14 shown in FIG. 6 in order to determine whether the pump cell 41 exhibits the oxygen removal function, in other words, in order to determine whether oxygen that oxidizes the sensor cell 42 exists in the measurement gas chamber 61. In FIG. 6, step S13 is a determination process based on the temperature Tp of the pump cell 41, and step S14 is a determination process based on the pump voltage Vp.

It is noted that, the monitor current Im increases in accordance with an amount of residual oxygen that the pump cell 41 has not removed. Therefore, the monitor current Im may be used for determining whether oxygen that oxidizes the sensor cell 42 exists in the measurement gas chamber 61. It is noted that, in a case where the monitor cell 43 is not activated, the monitor current Im indicates zero, and therefore, the temperature of the monitor cell 43 needs to be included in the condition for the determination.

Therefore, the SCU 31 of the present embodiment uses the temperature Tm of the monitor cell 43 instead of the temperature Tp of the pump cell 41.

Specifically, the temperature detector 311 of the SCU 31 shown in FIG. 2 detects the temperature Tm of the monitor cell 43 as the temperature of the sensor element 40. Specifically, the temperature detector 311 detects the monitor current Im when the AC voltage is applied to the electrodes 57 and 58 of the monitor cell 43. The temperature detector 311 computes the admittance Ym of the monitor cell 43 based on the detected monitor current Im and the applied AC voltage by using an arithmetic formula or the like. The temperature detection part 311 computes the temperature Tm of the monitor cell 43 based on the computed admittance Ym with reference to a map. In the present embodiment, the temperature Tm of the monitor cell 43 corresponds to the element temperature parameter. Note that the controller 310 may use the impedance Zm of the monitor cell 43 instead of the admittance Ym of the monitor cell 43.

Figure 9:
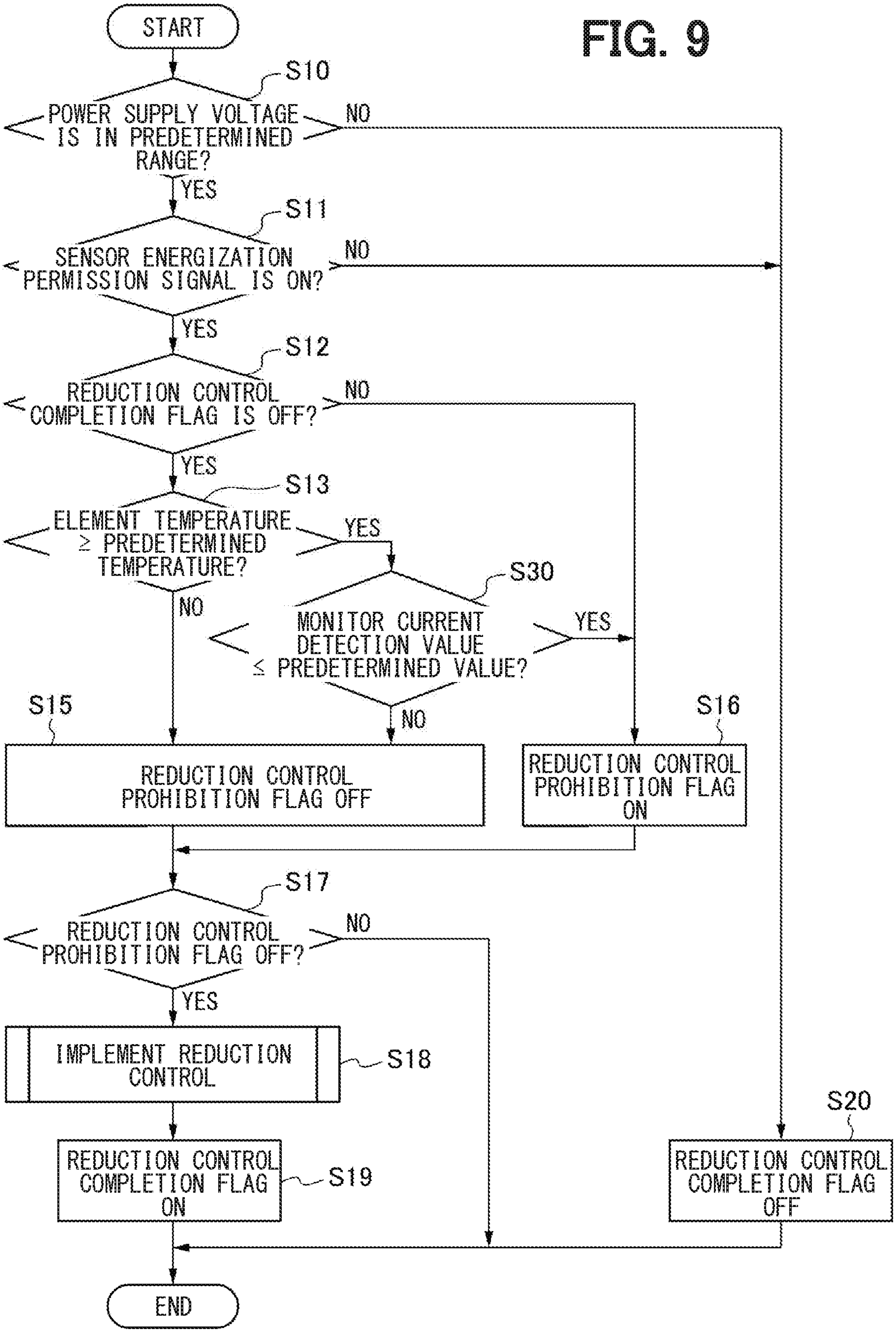
FIG. 9 is a flowchart showing a procedure of processing implemented by the SCU according to a second embodiment.

As shown in FIG. 9, the controller 310 of the present embodiment determines whether the element temperature is equal to or higher than a predetermined temperature in the process of step S13. Specifically, in the process of step S13, the controller 310 determines whether the temperature Tm of the monitor cell 43 detected by the temperature detector 311 is equal to or higher than a predetermined temperature Tmth. The predetermined temperature Tmth is set to a temperature that is the same as the temperature, at which the monitor cell 43 exhibits the oxygen removal function, or higher. In the present embodiment, the temperature Tm of the monitor cell 43 corresponds to an element temperature parameter.

As shown in FIG. 9, when the controller 310 makes an affirmative determination in the process of step S13, the controller 310 determines whether the monitor current detection value Im is less than or equal to a predetermined value Ith in the process of step S30. The predetermined value Ith is set in advance through an experiment or the like to enable the controller 310 to determine whether residual oxygen exists in the measurement gas chamber 61.

When the controller 310 makes an affirmative determination in step S30, that is, when the monitor current detection value Im is equal to or smaller than the predetermined value Ith, the controller 310 determines that the monitor cell 43 does not remove the residual oxygen. In this state, the residual oxygen does not exist in the measurement gas chamber 61, and therefore, the sensor electrode 56 is not oxidized. Therefore, implementation of the reduction control is not necessary. Thus, when the controller 310 makes an affirmative determination in the process of step S30, the controller 310 maintains the reduction control prohibition flag F20 in the on state in the process of step S16.

On the other hand, when the controller 310 makes a negative determination in step S30, that is, when the monitor current detection value Im exceeds the predetermined value Ith, the controller 310 determines that the monitor cell 43 removes the residual oxygen. In this state, the residual oxygen is present in the measurement gas chamber 61, and therefore, the sensor electrode 56 may be oxidized. Therefore, implementation of the reduction control is necessary. Thus, in a case where the controller 310 makes a negative determination in the process of step S30, the controller 310 sets the reduction control prohibition flag F20 to an off state in the process of step S15.

The gas sensor 21 of the present embodiment as described above enables to produce the operations and effects (4) and (5) as follows in place of the operations and effects (2) and (3) as described above.

(4) The controller 310 determines whether the monitor cell 43 exhibits the oxygen removal function in the determination process of step S13 and step S30 shown in FIG. 9. When the controller 310 makes an affirmative determination in the process of step S13 and makes an affirmative determination in the process of step S30, the monitor cell 43 does not exhibit the oxygen removal function. Therefore, the controller 310 determines that residual oxygen does not exist in the measurement gas chamber 61. In this case, the controller 310 determines that the pump cell 41 appropriately exhibits the oxygen removal function and that implementation of the reduction control is not necessary. Therefore, the controller 310 turns on the reduction control prohibition flag F20 in the process of step S16. This configuration enables to avoid implementation of the reduction control in a state where the sensor electrode 56 is not oxidized, and therefore, enables to avoid implementation of the unnecessary reduction control.

(5) The temperature detector 311 acquires the temperature Tm of the monitor cell 43 based on the admittance Ym or the impedance Zm of the monitor cell 43 when the AC voltage is applied to the electrodes 57 and 58 of the monitor cell 43.

This configuration enables to detect the temperature Tm of the monitor cell 43 with a simple configuration.

Third Embodiment

Subsequently, a third embodiment of the gas sensor 21 will be described. Hereinafter, a difference from the gas sensor 21 of the first embodiment will be mainly described.

Figure 10:
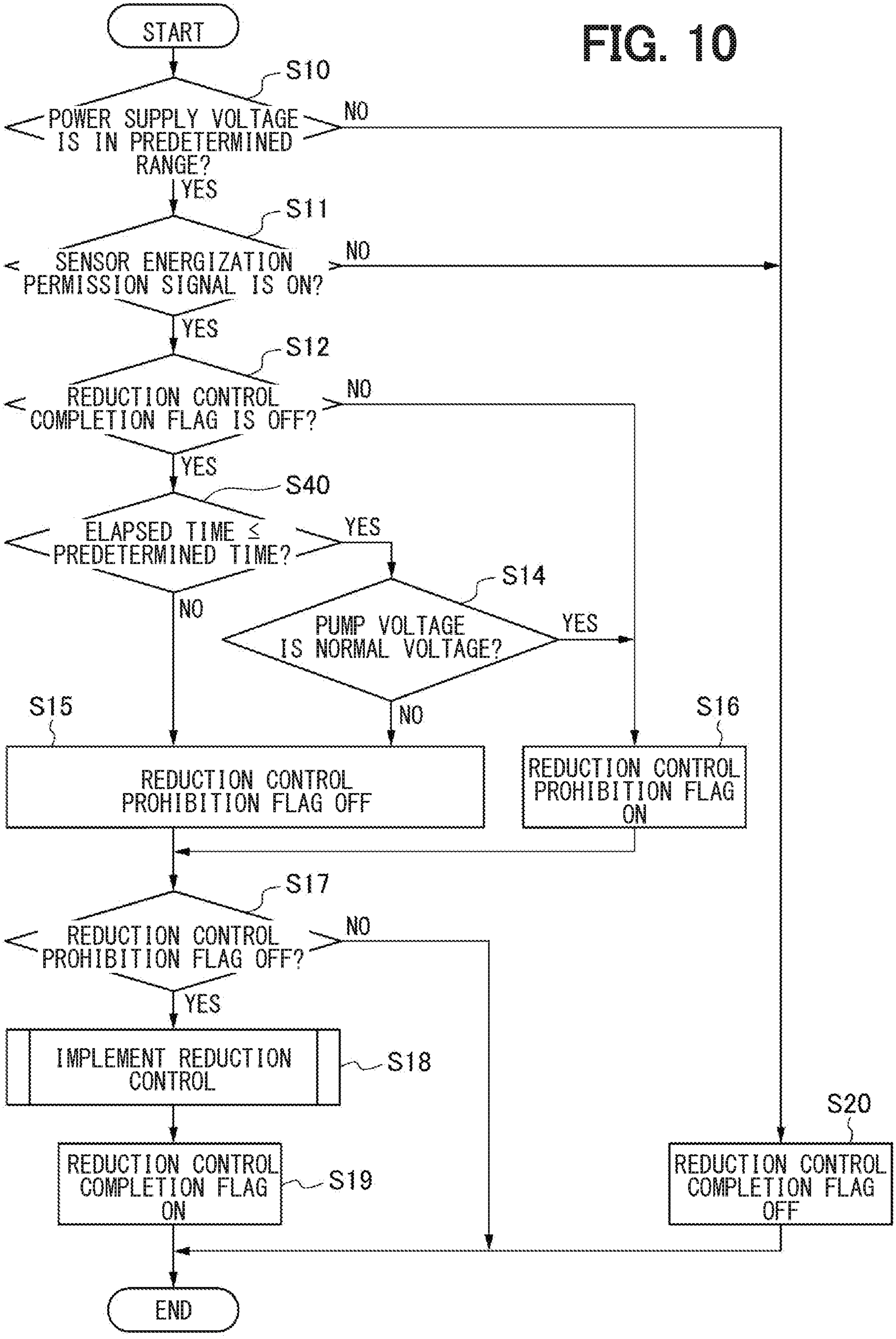
FIG. 10 is a flowchart showing a procedure of processing performed by the SCU according to a third embodiment.

As shown in FIG. 10, the controller 310 according to the present embodiment executes a process of step S40 instead of the process of step S13 shown in FIG. 6. In the process of step S40, the controller 310 determines whether an elapsed time Ts is less than or equal to a predetermined time Tsth. The elapsed time Ts is from when the power supply voltage Vbs of the SCU 31 becomes less than the predetermined voltage Vth20 until the power supply voltage Vbs becomes equal to or higher than the predetermined voltage Vth20. It physically takes time after the power supply voltage Vbs of the SCU 31 becomes lower than the predetermined voltage Vth20 until the temperature Tp of the pump cell 41 becomes lower than the predetermined temperature Tpth. In the present embodiment, the time period, which is after the power supply voltage Vbs of the SCU 31 becomes lower than the predetermined voltage Vth20 until the temperature Tp of the pump cell 41 becomes lower than the predetermined temperature Tpth, is measured through an experiment. The predetermined time Tsth is set to a time period that is same as or shorter than the measured time period. That is, in a case where the elapsed time Ts is equal to or shorter than the predetermined time Tsth, an estimation may be made that the temperature Tp of the pump cell 41 is equal to or higher than the predetermined temperature Tpth and that the pump cell 41 exhibits the oxygen removal function.

The gas sensor 21 of the present embodiment as described above enables to produce the operations and effects (6) as follows in place of the operations and effects (2) and (3) as described above.

(6) The controller 310 requires only to measure the elapsed time Ts after the power supply voltage Vbs becomes less than the predetermined voltage Vth20 until the power supply voltage Vbs becomes higher than or equal to the predetermined voltage Vth20 in the process of step S13. Therefore, the configuration enables to simplify the process compared with the process of step S13 shown in FIG. 6 that uses the temperature Tp of the pump cell 41.

Fourth Embodiment

Subsequently, a fourth embodiment of the gas sensor 21 will be described. Hereinafter, a difference from the gas sensor 21 of the first embodiment will be mainly described.

As indicated by the broken line in FIG. 2, the SCU 31 of the present embodiment further includes an operation state detector 312. The operation state detector 312 detects whether the engine 10 restarts after warming up. Specifically, when the engine 10 is restarted after implementation of the idling stop control, the engine ECU 35 notifies the SCU 31 of the restart. In response to the notification from the engine ECU 35, the operation state detector 312 detects that the engine 10 restarts after the warming up. When the operation state detector 312 detects that the engine 10 restarts after warming up, the operation state detector 312 notifies the controller 310 of the detection of the restart accordingly.

Figure 11:
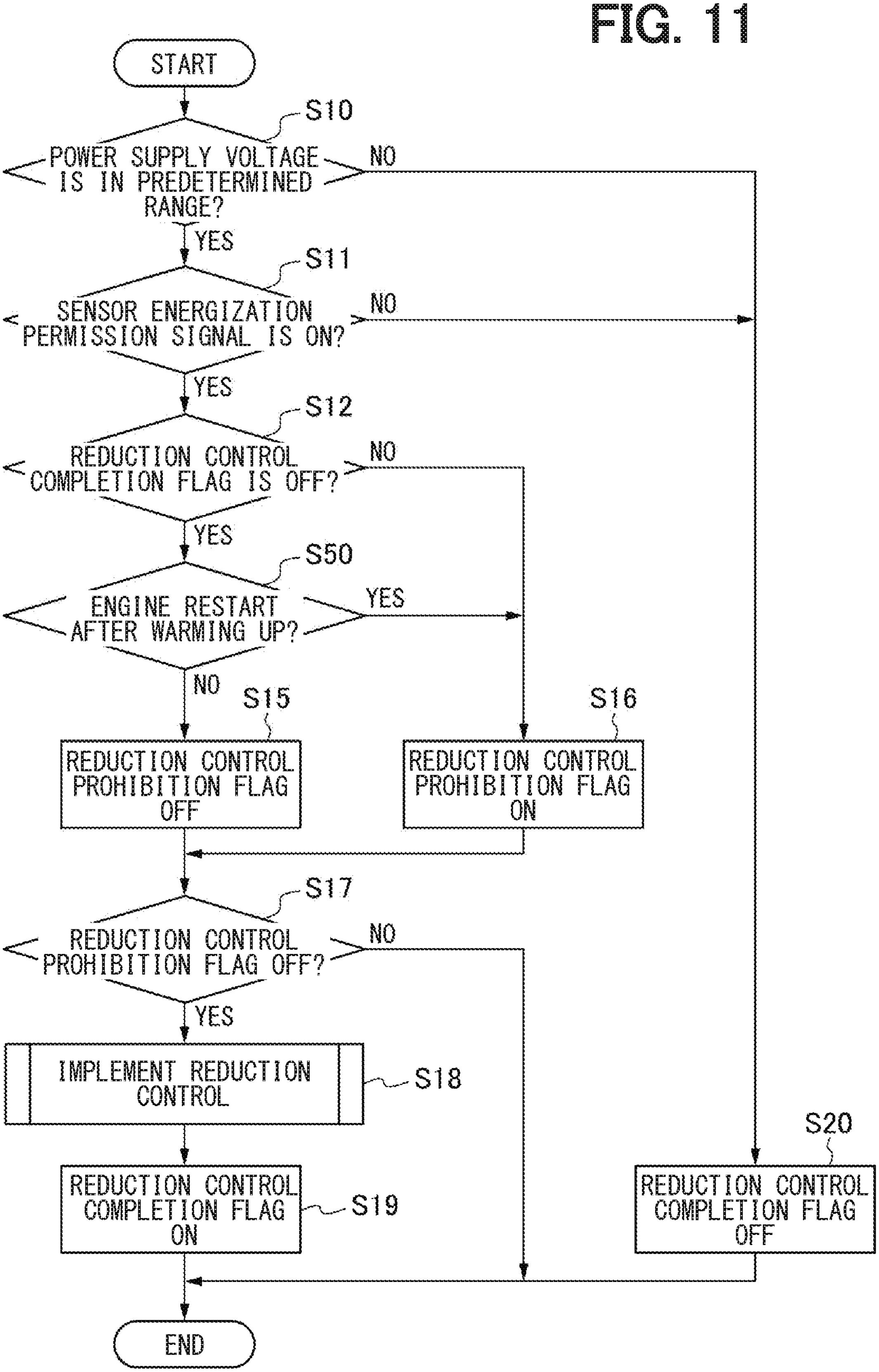
FIG. 11 is a flowchart showing a procedure of processing implemented by the SCU according to a fourth embodiment.

In addition, as shown in FIG. 11, the controller 310 of the present embodiment executes a process of step S50 instead of the processes of steps S13 and S14 shown in FIG. 6. The controller 310 determines whether the engine 10 restarts after warming up in the process of step S50. In a case where the controller 310 makes an affirmative determination in the process of step S50, the controller 310 sets the reduction control prohibition flag F20 to an on state in the process of step S16. Alternatively, in a case where the controller 310 makes a negative determination in the process of step S30, the controller 310 sets the reduction control prohibition flag F20 to an off state in the process of step S15.

The gas sensor 21 of the present embodiment as described above enables to produce the operations and effects (7) as follows in place of the operations and effects (2) and (3) as described above.

(7) The controller 310 requires only to determine whether the engine 10 restarts after warming up. Therefore, the configuration enables to simplify the process compared with the process of steps S13 and S14 shown in FIG. 6 that uses the temperature Tp of the pump cell 41 and the pump voltage Vp.

Other Embodiments

The embodiments described above may be implemented in the following forms.

From the gas sensor 21 of the first embodiment, the monitor cell 43 may be omitted in a case where the concentration of residual oxygen in the exhaust gas detected by using the sensor cell 42 is negligibly small. In his case, the gas sensor 21 may compute the NOx concentration based on the sensor current detection value Is.

The gas sensor 21 in each of the embodiments may includes an electrode for the pump cell 41, an electrode for the sensor cell 42, and an electrode for the monitor cell 43 separately in place of the common electrode 58.

The SCU 31 and the control method thereof described in the present disclosure may be embodied with one or more special computer provided with at least one processor and at least one memory programmed to execute one or more functions embodied with a computer program. The SCU 31 and the control method described in the present disclosure may be embodied with a special computer provided with at least one processor that includes at least one special hardware logic circuit. The SCU 31 and the control method thereof described in the present disclosure may be embodied with at least one special computer provided with a combination of a processor and a memory programmed to implement one or more functions and at least one processor provided with at least one hardware logic circuit. The computer program may be stored, as instructions executable by a computer, in a tangible non-transitory computer-readable medium. The special hardware logic circuit and the hardware logic circuit may be embodied with a digital circuit including multiple logic circuits or may be embodied with an analog circuit.

The present disclosure is not limited to the specific examples described above. The specific examples described above which have been appropriately modified in design by those skilled in the art are also encompassed in the scope of the present disclosure so far as the modified specific examples have the features of the present disclosure. Each element included in each of the specific examples described above, and the placement, condition, shape, and the like of the element are not limited to those illustrated, and can be modified as appropriate. The combinations of elements included in each of the above described specific examples can be appropriately modified as long as no technical inconsistency occurs.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A gas sensor control device comprising:

a first cell that includes a first electrode, which is provided in a measurement gas chamber configured to introduce gas to be detected, and a second electrode, which is provided in a reference gas chamber configured to introduce reference gas, wherein the first cell is configured, on application of a voltage between the first electrode and the second electrode, to apply the voltage on the gas to be detected to remove oxygen in the gas to be detected, wherein the first cell is a pump cell and the voltage between the first electrode and the second electrode is a pump voltage;

a second cell that includes a third electrode, which is provided in the measurement gas chamber, and a fourth electrode, which is provided in the reference gas chamber, wherein the second cell is configured, on application of a voltage between the third electrode and the fourth electrode, to cause a current to flow between the third electrode and the fourth electrode, wherein the current corresponds to a concentration of a specific gas component in the gas to be detected after the oxygen is removed by the first cell; and a controller configured to selectively implement a normal control, which is to apply a first voltage to the first electrode and the second electrode of the first cell in order to remove oxygen in the gas to be detected, and a reduction control, which is to apply a second voltage higher than the first voltage to the first electrode and the second electrode of the first cell in order to reduce the third electrode that is oxidized, wherein the controller is configured to determine whether implementation of the reduction control is necessary and to prohibit implementation of the reduction control on determination that implementation of the reduction control is not necessary based on the pump voltage being set to the first voltage.

2. The gas sensor control device according to claim 1, wherein the controller is configured to determine that implementation of the reduction control is not necessary on determination that the first cell exhibits an oxygen removal function.

3. The gas sensor control device according to claim 2, further comprising:

a temperature detector configured to detect an element temperature parameter indicating a temperature of a sensor element provided with the first cell and the second cell, wherein the controller is configured to determine that the first cell exhibits the oxygen removal function on determination that the element temperature parameter is equal to or higher than a predetermined value and that the normal control is executed.

4. The gas sensor control device according to claim 3, wherein the temperature detector is configured:

to detect a temperature of the first cell based on an admittance or an impedance of the first cell when an AC voltage is applied to the first electrode and the second electrode of the first cell; and to use the temperature of the first cell as the element temperature parameter.

5. The gas sensor control device according to claim 1, wherein the first electrode of the first cell and the third electrode of the second cell are provided in the same measurement gas chamber.

6. The gas sensor control device according to claim 1, wherein the controller is configured to implement the reduction control on determination that implementation of the reduction control is necessary based on the pump voltage not being set to the first voltage.

7. The gas sensor control device according to claim 1, further comprising:

a temperature detector configured to detect an element temperature parameter indicating a temperature of a sensor element provided with the first cell and the second cell, wherein the controller, the first cell, and the second cell are configured to start when a power supply voltage of the controller, the first cell, and the second cell reaches a voltage threshold, and the controller is configured to, when the power supply voltage drops once and thereafter increases to the voltage threshold, and on determination that the element temperature parameter is equal to or higher than a predetermined value and that the pump voltage is set to the first voltage, determine that the normal control is implemented, that the first cell exhibits an oxygen removal function, and that implementation of the reduction control is not necessary.

8. The gas sensor control device according to claim 1, wherein the first voltage is set such that a concentration of oxygen in the measurement gas chamber is equal to or less than a predetermined concentration.

9. A gas sensor control device comprising:

at least one processor configured:

to implement a normal control to apply a first voltage to a first electrode in a measurement gas chamber and a second electrode in a reference gas chamber in order to remove oxygen in gas to be detected in the measurement gas chamber, wherein a pump cell includes the first electrode and the second electrode and a voltage between the first electrode and the second electrode is a pump voltage;

to apply a detection voltage between a third electrode in the measurement gas chamber and a fourth electrode in the reference gas chamber to cause a current between the third electrode and the fourth electrode and to detect, based on the current, a concentration of a specific gas component contained in the gas to be detected from which the oxygen is removed by the normal control;

to implement, alternatively to the normal control, a reduction control to apply a second voltage higher than the first voltage to the first electrode and the second electrode in order to cause a reduction reaction in the third electrode that is oxidized; and to determine whether implementation of the reduction control is necessary and to prohibit implementation of the reduction control on determination that implementation of the reduction control is not necessary based on the pump voltage being set to the first voltage.

10. The gas sensor control device according to claim 9, wherein the at least one processor is configured to implement the reduction control on determination that implementation of the reduction control is necessary based on the pump voltage not being set to the first voltage.

11. The gas sensor control device according to claim 9, further comprising:

a temperature detector configured to detect an element temperature parameter indicating a temperature of a sensor element provided with a first cell and a second cell, wherein the at least one processor, the first cell, and the second cell are configured to start when a power supply voltage of the at least one processor, the first cell, and the second cell reaches a voltage threshold, and the at least one processor is configured to, when the power supply voltage drops once and thereafter increases to the voltage threshold, and on determination that the element temperature parameter is equal to or higher than a predetermined value and that the pump voltage is set to the first voltage, determine that the normal control is implemented, that the first cell exhibits an oxygen removal function, and that implementation of the reduction control is not necessary.

12. The gas sensor control device according to claim 9, wherein the first voltage is set such that a concentration of oxygen in the measurement gas chamber is equal to or less than a predetermined concentration.

13. A method implemented by at least one processor, comprising:

implementing a normal control to apply a first voltage to a first electrode in a measurement gas chamber and a second electrode in a reference gas chamber in order to remove oxygen in gas to be detected in the measurement gas chamber, wherein a pump cell includes the first electrode and the second electrode and a voltage between the first electrode and the second electrode is a pump voltage;

applying a detection voltage between a third electrode in the measurement gas chamber and a fourth electrode in the reference gas chamber to cause a current between the third electrode and the fourth electrode and to detect, based on the current, a concentration of a specific gas component contained in the gas to be detected from which the oxygen is removed by the normal control;

implementing, alternatively to the normal control, a reduction control to apply a second voltage higher than the first voltage to the first electrode and the second electrode in order to cause a reduction reaction in the third electrode that is oxidized; and determining whether implementation of the reduction control is necessary and to prohibit implementation of the reduction control on determination that implementation of the reduction control is not necessary based on the pump voltage being set to the first voltage.

14. The method according to claim 13, further comprising:

implementing the reduction control on determination that implementation of the reduction control is necessary based on the pump voltage not being set to the first voltage.

15. The method according to claim 13, further comprising:

detecting an element temperature parameter indicating a temperature of a sensor element provided with a first cell and a second cell, wherein starting the at least one processor, the first cell, and the second cell when a power supply voltage of the at least one processor, the first cell, and the second cell reaches a voltage threshold, and determining that the normal control is implemented, that the first cell exhibits an oxygen removal function, and that implementation of the reduction control is not necessary, when the power supply voltage drops once and thereafter increases to the voltage threshold, and on determination that the element temperature parameter is equal to or higher than a predetermined value and that the pump voltage is set to the first voltage.

16. The method according to claim 13, wherein the first voltage is set such that a concentration of oxygen in the measurement gas chamber is equal to or less than a predetermined concentration.

* * * * *